United States Patent [19]

Gould

[11] Patent Number: 5,010,020

[45] Date of Patent: Apr. 23, 1991

[54] QUICK COLOR TEST TO DETECT LEAD RELEASE FROM GLAZE AND ENAMEL COATINGS

[75] Inventor: John H. Gould, Silver Spring, Md.

[73] Assignee: The United States of America as represented by the Department of Health and Human Services, Washington, D.C.

[21] Appl. No.: 418,283

[22] Filed: Oct. 6, 1989

Related U.S. Application Data

[63] Continuation-in-part of Ser. No. 264,041, Oct. 28, 1988, Pat. No. 4,873,197.

[51] Int. Cl.$^5$ .............................................. G01N 31/22
[52] U.S. Cl. ........................................ 436/77; 422/56; 422/61; 436/74; 436/169; 436/177; 436/178
[58] Field of Search ................. 436/77, 164, 169, 174, 436/177, 178, 74, 182; 422/56, 61

[56] References Cited

U.S. PATENT DOCUMENTS

| | | | |
|---|---|---|---|
| 3,397,964 | 1/1965 | Zall | 422/56 |
| 3,809,537 | 5/1974 | Horine | |
| 3,893,808 | 8/1975 | Campbell | |
| 3,934,976 | 1/1976 | Zelaskowski | |
| 3,955,927 | 5/1976 | Zelaskowski et al. | |
| 4,244,693 | 1/1981 | Guon | 436/164 |
| 4,873,197 | 10/1989 | Gould | 436/77 |

FOREIGN PATENT DOCUMENTS 61-296241 12/1986 Japan .

OTHER PUBLICATIONS

Gould, J. H. and Capar, S. G., "A Quick Color Test to Detect Lead Release From Glazed Ceramic and Enameled Metalware," Analytical Letters 21(11) 2145–2154 (1988).
"Spot Tests in Inorganic Analysis" by Fritz Feigl et al, sixth English edition, translated by Ralph E. Oesper, pp. 282–287; (1982).
Feigl, Laboratory Manual of Spot Tests, Academic Press, NY 1948, p. 217.
Feigl et al, "Spot Tests in Inorganic Analysis": Elsevier Publishing Co. NY (1972) p. 569.

*Primary Examiner*—Robert J. Warden
*Assistant Examiner*—Jill Johnston
*Attorney, Agent, or Firm*—John E. Tarcza

[57] ABSTRACT

A color test is presented for the purpose of quickly identifying glaze or enamel coatings which releases excessive Pb. Citric acid solution on filter paper is used to extract Pb from the coatings and a Pb sensitive chromogen indicates the presence of Pb on the paper. The quick color test takes approximately 30 minutes to complete. The kits are also provided for determining whether excessive Pb is present in a glaze or enamel coating.

22 Claims, No Drawings

QUICK COLOR TEST TO DETECT LEAD RELEASE FROM GLAZE AND ENAMEL COATINGS

CROSS-REFERENCE TO RELATED APPLICATIONS

The present application is a Continuation-in-Part of copending application Ser. No. 07/264,041 filed on Oct. 28, 1988, now U.S. Pat. No. 4,873,197, the entire contents of which are hereby incorporated by reference.

FIELD OF THE INVENTION

The present invention relates to a test method and test kit to be used for quickly identifying glazed and/or enameled coatings which release excessive amounts of lead (Pb). More specifically, the invention is directed to a method of using a filter paper containing a solution of citric acid to extract Pb from glaze and enamel coatings so that a Pb sensitive chromogen indicates the presence of lead on the paper.

BACKGROUND OF THE INVENTION

Lead components have long been used to impart many desirable properties in glaze and enamel compositions for numerous substrates including dinnerware. Unfortunately, improperly formulated or improperly fired lead glazes or enamels allow hazardous levels of Pb to be released from such substrate surfaces.

The Food and Drug Administration (FDA) has established action levels for maximum Pb release from earthenware (Table 1). Such earthenware determined to have a lead content at or above these levels will be subject to possible regulatory action by the FDA. The FDA monitors both domestically produced and imported dinnerware on a routine basis. The AOAC (Association of Official Analytical Chemists) or equivalent ASTM (Annual Book of ASTM Standards (1987) 15.02, 314–316) test methods for Pb are used in the United States. Both of these methods require extraction (leaching) of 6 pieces of ware for 24 hours with 4% acetic acid at room temperature. This leach solution is analyzed for Pb by flame atomic absorption spectroscopy.

TABLE 1

| Current FDA Action Levels for Maximum Pb Released from Earthenware | | |
|---|---|---|
| Category | Action Basis | Action Level ($\mu$g Pb/ml) |
| Flatware | Average of 6 units | 7 |
| Small hollowware (<1.1 L) | Any one of 6 units | 5 |
| Large hollowware (>1.1 L) | Any one of 6 units | 2.5 |

A representative test technology is exemplified by U.S. Pat. No. 3,809,537, of which Example 17 is typical. Dinnerware tested with this technology is leached by a solution of acetic acid in water (or as in the patent, white vinegar) for various periods of time ranging from 30 minutes to 24 hours. The process of this patent requires a 24 hour leach period which saves no time relative to the Official Methods of Analysis, sec. 25.024–.027, 14th ed. (1984) pub. by AOAC) and is qualitative at best. Other methods claim results after only 30 minutes of contact. (See Official Methods of Analysis, sec. 25.028–25.030).

This short-term leach method requires extensive chemical operations, such as the adjustment of hydrogen ion concentration, the extraction by an immiscible solvent containing the complex, and an estimation of the depth of color produced. Some of these methods are viewed as being quantitative. These extensive operations are required because the large volumes of acetic acid solutions required to fill the test vessel dilute the lead released and for that reason, a very sensitive and complex method is required.

SUMMARY OF THE INVENTION

An object of the present invention is to provide a method to determine within thirty minutes or less if a glaze or an enamel coating is releasing excessive amounts of toxic lead.

Another object of the invention is to provide a simple test to determine if a glaze or an enamel coating is releasing excessive amounts of toxic lead, so that the test can be applied in shipping sheds, in warehouses, at dockside, or in a laboratory to preselect certain glaze or enamel coated items for a full-scale 24 hour leach test.

Still another object of the invention is to develop a prescreening procedure of lead-releasing glaze or enamel coated substrates so that only those items initially determined to have a greater likelihood of being unsafe are subjected to a full-scale 24 hour leach test.

Yet another object of the invention is to provide a method to test specific parts of decorations and colored glazes when present on a glazed or enameled item separately so as to pinpoint, if desired, the exact source from which lead is being released from a coating without increasing the time needed to perform the test.

A further object of the invention is to provide a simple method for testing lead release in the home from glaze and enamel coatings with which consumers are in contact every day and/or are in everyday use.

A still further object is to provide a test kits which will enable one to easily practice the method of the present invention.

These and other objects of the present invention are generally accomplished by providing a slip of filter paper which is wet with a solution of citric acid or formic acid. This filter paper is contacted with a glaze or enamel coating so as to extract soluble Pb from the glazed or enameled coating. After approximately thirty minutes, the filter paper is spotted with a chromogen. The immediate formation of a rose to rose/red stain indicates that presence of excessive Pb.

The method and kit provided herein can be used, for example, in a method for determining the presence of excessive amounts of lead on an area of a glazed ceramic or an enameled metal ware, by extracting lead from the coating by contacting the coated ware with a filter paper containing formic and/or citric acid, spotting the filter paper with a chromogen, and detecting a change in color of the filter paper.

Such a method could further comprise subjecting the ware to a full scale leaching procedure if so desired.

The filter paper can contain a solution of citric acid or formic acid. The concentration is preferably in the range of about 3 to about 5% V to Wt. or V to V as monobasic acids, and more preferably, the concentration is about 4% V to Wt. or V to V as monobasic acids.

In the method of the present invention, the filter paper is preferably spotted with the chromogen from about 10 minutes after the filter paper has contacted a coated substrate to about 30 minutes after the filter paper has contacted a coated substrate.

The quick color test (QCT) method of the invention is sufficiently simple so that it may be applied to screen items such as dinnerware in shipping sheds, warehouses, or at dock-side was well as in a laboratory. Optimal preselection of dinnerware for analysis by the 24 hour AOAC/ASTM method utilizes laboratory and investigative resources more efficiently by limiting the rigorous 24 hour AOAC/ASTM examination to ware which has a greater likelihood of being unsafe.

DETAILED DESCRIPTION OF THE INVENTION

Certain aspects of the present invention as discussed herein are in terms of detecting lead in glaze or enamel coatings which are on dinnerware. The same is a preferred embodiment of the present invention, but should not be construed to limit the present invention, inasmuch as the present invention is to only be limited by the scope of the appended claims.

The first step of the inventive method disclosed herein involves extracting soluble Pb from test glazes and/or enamel coatings. This result is achieved by contacting the test glaze and/or enamel coating with a slip of filter paper wet with a solution of citric acid or formic acid. After this, preferably from about 10 to about 30 minutes later, the paper slip is spotted with a chromogen. (See F. Figel, "Spot Tests in Inorganic Analysis", pp. 73-74 (1958)). The instant formation of a rose to rose/red stain signifies that the tested coating contains an excessive amount of lead. Consequently, these tested coatings will have a greater likelihood of containing dangerous amounts of lead as judged by a full-scale 24 hour leach test. The present invention provides an efficient and simple preselection procedure whereby only those tested coatings having a greater lead release are subjected to the fullscale leach test.

This proposed test method concentrates the lead ions that are released from the test surface under acid conditions in about 30 minutes or less into paper slips and not into a large volume of solvent. The final concentration in the paper is dependent only upon the rate of release of the lead ions. The final color developed in these test slips is qualitatively dependent upon the quantity of lead ion present. Various decorations, or parts of decorations and individual glazes, colored or clear, if present on a substrate, can be sampled individually so as to determine the exact source of any lead that might be released without materially increasing the total time for the test. The area resolution of this test and the colored complex formed have been found to be sufficiently precise that the exact shape of the lead releasing source can be determined. This visualization can enable manufacturers to survey their products and eliminate all sources of soluble lead on the finished product surfaces.

The rapidity and the ease with which this test can be conducted permits it to be applied at the repositories of commercial dinnerware, such as shipping sheds and dock-side warehouses. Such applications would eliminate the current practice of randomly selecting glazed and enameled substrates for removal to analytical laboratories for testing by designating at once those articles that are of questionable safety. This preselection, therefore, will make the entire analytical laboratory operation much more efficient.

All reagents used in the present method are ACS Reagent Grade. Preferably, a 1.3% citric acid solution is used, and this solution is prepared by dissolving 1.33 g of citric acid in 100 ml of distilled water. The preferred chromogen solution is in a 0.2% solution, prepared by dissolving 0.05 g rhodizonic acid dipotassium salt (#2942 of Eastman Kodak Co., Rochester, N.Y., or any equivalent) in 25 ml of distilled water. This solution should be stored in the dark. A new solution should be prepared every three days or when the solution no longer gives a bright yellow stain when a drop is applied to neutral filter paper. The filter paper can be Whatman #1 chromatographic paper, or Schleicher and Schuell white ribbon #589, or any equivalent. The filter paper is preferably cut into $2\times2$ cm pieces.

In the Examples which follow, dinnerwares were tested for excess lead. The procedure used to test the wares is indicative of testing procedures for other substrates. The samples to be tested are prepared by cleaning each piece of ware with a detergent wash. The detergent wash is formulated by adding 15 g of alkaline detergent (for example, Calgonite of Calgon Corp., Pittsburgh, PA or an equivalent) to 1 gallon of distilled water. The samples can also be wiped with a clean cloth, as this may be all that is available at a dockside warehouse, where testing on wares for lead might be performed.

One or more filter paper slips is placed on a clean, dry, smooth, horizontal, food contact surface of the ware to be tested. Each slip is wetted with about 75 $\mu l$ of citric acid solution. The paper must be soaked, not just moist, but there must be little or no excess solution present. The slip must be in complete contact with the surface (i.e., no ridges or bubbles). All colors that would be accessible to the AOAC acetic acid leaching should be tested.

After the wet paper slip has been in contact with the ware for about 30 minutes (or sooner if the slip becomes dry), it is removed from the ware and placed on a clean white surface. The slip is then spotted with 5 $\mu l$ of chromogen solution. The appearance of a rose to a rose/red stain on the paper slip indicates the presence of Pb. The color of the Pb complex is best viewed against a white background such as a porcelain plate, a teflon dish or other white water-proof surface.

Both formic and citric acid can be used. Citric acid is preferred because it is nonvolatile and thus is less affected by drying if the application of the chromogen to the paper slip is delayed.

The present test method is not sensitive to cadmium, the other toxic element determined by the AOAC-/ASTM leach method. However, the presence of cadmium should be presumed if the glaze, enamel, or decorations are yellow, orange, or red in color. There are other pigments which can produce these colors, but ware having these colors should be analyzed by the AOAC/ASTM method for Cd independent of the outcome of the present QCT for Pb.

The sensitivity of the present test was determined by pipetting Pb standard solutions (in 4% citric acid) onto $2\times2$ cm filter paper slips and spotting the slips with chromogen solution. The minimum detectable amount of Pb was 0.25 $\mu g/cm^2$. The maximum amount tested was 5 $\mu g/cm^2$.

Of all the ions reported by Feigl and Suter (Ind. and Eng. Chem. Anal. Ed. (1942) 14, 840-42) which produce colored complexes that might be confused with the Pb complex, only Ba and Cd are found in glazes, enamels, or decorations. These ions give red-brown and brown-red complex colors, respectively, in dilute acid media. Both Ba and Cd were dissolved in citric and formic acid solutions and applied to paper slips at a concentration of 1.25 $\mu g/cm^2$. No color developed when these dried slips were treated with the chromogen solution.

Stannous ion is a third possible interference which gives a violet complex color. Stannous ion is probably not present in a finished coating because it is converted to the stannic ion by the firing process. Stannic oxide is often added as an opacifying agent to glazes and decorations but its solubility is expected to be very low in the dilute acid medium used to extract the surfaces.

The influence of the contact time between the paper slip and the ware on the intensity of the complex color was studied by applying 3 QCT paper slips to each piece of ware and successively developing the color on the slips after 5, 10, and 30 minutes, respectively. (Each paper slip was wetted with about 75 $\mu$l of the citric acid solution as discussed above). Each of the 3 slips was applied to the same type of area (or decoration) on the ware. Thirty-three different sets (6 pieces/set, except one 3 piece/set) of ware were found to form a positive QCT at least after the maximum 30 minute contact period. Of these sets, 30 were decorated ware (177 pieces) and 3 were plain ware (18 pieces). The average subjective intensity of the complex color was estimated on a scale from 0 (no color) to 5 (very deep rose/red). Using these values, the average increase in color intensity over the 5 minute contact time was calculated for each piece of decorated and plain ware. The decorated ware's average increase in intensity over the 5 minute test was 17% and 38% for the 10 and 30 minute periods, respectively. The plain ware's average increase in intensity was also 17% and 37% for the 10 and 30 minute periods, respectively. Due to the greater color intensity obtained, a 30 minute contact time is preferred. However, a contact time of 10 minutes may be sufficient for testing of decorations on ware.

One requirement of a screening method is positive identification of those items requiring more thorough testing. It is extremely difficult to correlate qualitative results from the invention with quantitative results of the AOAC/ASTM method. Metal ion release is a function of both time and the releasing solution which are different for these test methods. The present test measures Pb released from a small area into a small volume of citric acid in a short period of time, whereas the AOAC/ASTM method measures Pb released from a large area into a large volume (relative to the strip) of dilute acetic acid over a long period of time.

Another difficulty arises from Pb containing decorations on the food contact surface of the ware. Painted decorations, decals, or colored glazes added to finish the ware require firing of the ware a second or even a third time, and usually at a lower temperature than was used to first fuse the background glaze. If this low temperature firing is improperly performed, such decorations tend to release Pb more readily. The contributions of Pb from such decorative areas are functions of the manufacturing practice and the total area the decorations occupy. The AOAC/ASTM method will leach all decorations on the food contact surface whereas the present method will only test decorations to which it is applied. In addition, the present method may indicate high Pb release from a particular decoration but the AOAC/ASTM method may not confirm Pb excessive due to its larger dilution volume. An advantage of applying the present test to decorations is the identification of Pb releasing decorations; occasionally an exact colored complex image of the Pb releasing portion of the decoration will appear. Generally, the process of the invention will not deface good quality ware.

In view of the above, a purely empirical means of proving the reliability of the QCT was obtained by testing ware with both the QCT and the AOAC/ASTM methods. In order for the QCT to be useful, a positive QCT finding must indicate that the ware releases Pb near or over the FDA Action Level when tested by the AOAC/ASTM method. In addition, and more importantly, a negative QCT finding must indicate that the ware does not release Pb above the Action Level.

EXAMPLES

The present invention will be exemplified by the presentation of the following Examples, but should not be construed as being limited thereto.

The present QCT and AOAC/ASTM tests were applied to 67 sets of ware (6 pieces/set, except two 3 pieces/set). The color intensity of the complex formed was estimated on a scale ranging from no color to a very strong rose/red color. A 5, 10 and 30 minute contact time was used for this evaluation. The QCT paper slips were applied to decorations when they occurred on the food contact surface. If no decorations were present, the slip was applied to the glaze or enamel of the food contact surface. After the QCT, each piece of ware was analyzed by the AOAC/ASTM method.

The present test slips were cut into 2×2 cm pieces, and they were wetted with 75 $\mu$l of citric acid solution, as discussed previously. Each slip was spotted with 5 $\mu$l of the chromogen solution as discussed above.

Decorated Ware Results

The QCT and the AOAC/ASTM methods were performed on 51 sets of decorated ware. The QCT produced 32 positive findings and 19 negative findings. The 19 negative QCT sets were also negative (i.e., average <1 $\mu$g Pb/ml) by the AOAC/ASTM method. By the AOAC/ASTM method, 14 of the 32 positive QCT sets had Pb levels above the appropriate Action Level. Nine of the remaining 18 positive QCT set had average Pb levels ranging from 0.6 to 4.4 $\mu$g Pb/ml but all were below the appropriate Action Level due to the influence of the ware's shape and the relationship of surface area wet to volume. All 9 sets had at least two pieces in the set with levels $\geq$1 $\mu$g Pb/ml, and 4 had levels $\geq$2.5 $\mu$g Pb/ml. The remaining 9 QCT positive sets were <1 $\mu$g Pb/ml hence negative by the AOAC/ASTM method. This was probably due to the Pb release from a localized decoration.

All sets of ware identified by the AOAC/ASTM method to be above the Action Levels were positively identified by the QCT. Overall, the QCT correctly categorized 65% of the sets of ware as being above or below the Action Level. All incorrectly categorized sets were false positives. The QCT false positives are thought to occur because of the localized release of Pb by the decorations and dilution of Pb to below the Action Level.

One of the QCT positive findings resulted in a very weak color even though the AOAC/ASTM findings was relatively high. This ware was highly decorated with many different colors of glaze but the QCT paper slips had been applied to only one of the colors. This suggests that the QCT was applied to a decorated area that was not releasing the bulk of the Pb. Therefore, for the QCT to reliably detect excessive Pb release, all colored food contact areas of multi-colored ware should be tested.

Plain or Undecorated Ware

The QCT and the AOAC/ASTM methods were performed on 16 sets of plain ware (6 pieces/set). The QCT produced 3 positive findings and 13 negative findings. The 3 QCT positive findings were also positive by the AOAC/ASTM method. The 13 negative QCT sets were also negative by the AOAC/ASTM method. With respect to the Action Levels, the QCT correctly categorized 100% of the sets of undecorated ware. One QCT negative finding gave an AOAC/ASTM finding of about 0.8 μg Pb/ml (volume of ware=300 ml). This Pb level is below the quantitation limit of the AOAC/ASTM method (without applying the concentration option) and may also indicate the lower limit of the QCT for small hollow ware (<300 ml).

It has been observed that the moistened QCT must be in good contact with the surface in order to extract the Pb properly. QCT results on rough or textured surfaces may not be reliable and must be leached by the AOAC/ASTM method.

Comparison of Individual Ware Findings

Because the Action Levels are based on the findings of 6 pieces of ware, some information on the accuracy of the QCT is lost when solely comparing the QCT findings to these sets. To more precisely evaluate the analytical ability of the QCT, the QCT findings of each individual piece of ware were compared to its corresponding finding by the AOAC/ASTM method.

Analytical findings from the contact time experiment discussed above were used for this evaluation which allowed comparison of 5, 10, and 30 minute contact times. One slip of paper for the QCT was used for each timed contact on each 96 pieces of plain ware and 300 pieces of decorated ware. Since 2.5 μg Pb/ml is the lowest Action Level, a correct QCT finding was assumed to occur when the QCT gave a colored complex and the AOAC/ASTM finding was ≧2.5 μg Pb/ml. A correct QCT comparison was also assumed when the QCT was colorless and the AOAC/ASTM finding was <2.5 μg Pb/ml.

For the decorated ware, the QCT gave a correct response in 75, 74, and 71% of the cases for the 5, 10, and 30 minute contact time, respectively. For the plain ware, the QCT gave a correct response in 99, 98, and 98% of the cases for the 5, 10, and 30 minute contact time, respectively. There appears to be little difference in reliability of the QCT between the different contact times for plain ware even though the color intensity was greater after 30 minutes, as discussed earlier. However, there is less reliability in the QCT for decorated ware than plain ware. Many of the incorrect QCT positive findings for decorated ware had Pb levels below detection by the AOAC/ASTM method. As mentioned earlier, these QCT false positive findings are probably due to the Pb released by a decoration being diluted by the relatively large volume used by the AOAC/ASTM method.

The quick color test of the invention has been shown to reliably indicate the excessive release of Pb from glazes and enamels in less than 30 minutes. The quick color test is sufficiently sensitive to permit the preselection of ware for the full 24 hour AOAC/ASTM leach test with the expectation that Pb will be found in the leach solution. Application of the QCT to decorated ware requires that a sufficient number of slips be applied to each piece to test each decoration and each color of glaze. Plain, undecorated ware can be tested with one or two slips on the glaze. The QCT should be applied to the food contact surface for 30 minutes although 10 minutes is usually sufficient to test ware decorations. The test appears to be sufficiently simple that it can be applied outside the laboratory (e.g., in warehouses) to preselect ware for the 24 hour AOAC/ASTM test.

Test Kits for Performing the Methods of the Present Invention

The present invention also provides for a test kit useful in performing a quick analysis for lead utilizing the method of the present invention. A test kit advantageously it is thought should at least comprise the following:

(1) precut disks or strips of filter paper or a similarly absorbent paper article;
(2) an aqueous solution of a suitable acid, such as citric acid, formic acid, or a mixture thereof;
(3) distilled or deionized water; and
(4) rhodizonic acid dipotassium salt, or a similar chromogen which visibly changes colors in the presence of excessive lead.

It is noted that in such a kit, a solution of a chromogen like rhodizonic acid dipotassium salt, which is only stable for several days could be prepared with the distilled or deionized water just before testing of a substrate is to be performed. In such a manner possible problems with the instability of chromogen solutions could be overcome.

Alternatively, if a chromogen is used which can form relatively stable solutions, a kit could advantageously be prepared which comprises the following:

(1) precut disks or strips of filter paper or a similarly absorbent paper article;
(2) an aqueous solution of a suitable acid, such as citric acid, formic acid, or a mixture thereof; and
(3) an aqueous solution of a chromogen, which visibly changes colors in the presence of lead.

A kit as encompassed herein could also comprises additional materials useful in the analysis for lead by the present invention, if so desired. Such additional materials might include a color coded strip for comparison of results. The kit might also comprise containers for mixing or measuring solutions and solids which are present in the kit. These additional embodiments of the present invention, as well as certain others, such as applicators for applying solutions to a filter disk or similar paper article are considered readily understood by those skilled in the art. When a kit is prepared for sale, each of the chemical reagents is stored in a suitable container such as a glass or plastic vial and the vials together with the absorbent material such as absorbent paper are packaged in a box.

Such a kit as provided herein could be used outside the laboratory, including the home. The home use of the kit would be valuable in testing glaze and enamel coatings already in the surroundings of the consumer.

The QCT method herein disclosed is not sensitive to Cd, the other toxic element routinely tested for excessive release from glazed and enameled coatings. Cadmium based glazes, enamels, or decorations are either shades of yellow, orange, or red. Therefore, coatings with these colors should be tested by the AOAC/ASTM method for excessive Cd release. A kit as provided herein, if desired, could also provide information to a consumer on where and how such testing could be performed on such an article.

It is also noted herein that one could advantageously perform the first portion of the test method of the present invention (i.e., remove lead from a glaze or enamel coating utilizing an appropriate acidic solution and filter paper) and then allow a lag time to pass before contacting an appropriate chromogen (or chromogen containing solution) therewith. By utilizing such a lag time between extracting excessive lead in a coating onto an appropriate paper article, and the application thereto of a chromogen, one could provide for the centralized application of chromogen to sample paper disks, strips, squares, etc. For example, such a centralized location might be a laboratory setting, and test samples might be mailed or hand-delivered to the same.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. A kit for detecting the presence of excessive lead in a glaze or enamel coating, the kit comprising:
   precut pieces of an absorbent paper;
   an aqueous solution of a suitable acid;
   distilled or deionized water; and
   a chromogen which visibly changes colors when excessive lead is present in said coating.

2. The kit of claim 1, wherein said acid is citric acid, formic acid, or a mixture thereof.

3. The kit of claim 1, wherein said chromogen is rhodizonic acid dipotassium salt.

4. The kit of claim 3, wherein said acid is citric acid.

5. A kit for detecting the presence of excessive lead in a glaze or enamel coating, the kit comprising:
   precut pieces of an absorbent paper;
   an aqueous solution of a suitable acid; and
   a stable aqueous solution of a chromogen which visibly changes colors when excessive lead is in said coating.

6. The kit of claim 5, wherein said acid is citric acid, formic acid, or a mixture thereof.

7. A method for determining the presence of excessive amounts of lead in a surface, which comprises:
   extracting lead from said surface by contacting said surface with an absorbent material containing a solution of a material selected from the group consisting of formic acid, citric acid, and mixtures thereof;
   spotting said absorbent material with a chromogen; and
   detecting a change in colors of said absorbent material.

8. The method of claim 7, which further comprises subjecting any said surface, wherein a positive spot test is indicated, to a full scale leaching procedure to quantitate the amount of lead therein.

9. The method of claim 7, wherein said absorbent material contains a solution of citric acid.

10. The method of claim 7, wherein said absorbent material contains a solution of formic acid.

11. The method of claim 7, wherein said absorbent material is spotted with said chromogen about thirty minutes after said absorbent material has contacted said surface.

12. The method of claim 7, wherein said absorbent material is spotted with said chromogen about ten minutes after said absorbent material has contacted said surface.

13. The method of claim 9, wherein said citric acid is at a concentration of about 4% volume to weight as a monobasic acid.

14. The method of claim 10, wherein said formic acid is at a concentration of about 4% volume to weight or volume to volume as a monobasic acid.

15. The method of claim 9, wherein said citric acid is at a concentration of about 3% to about 5% volume to weight as a monobasic acid.

16. The method of claim 10, wherein said formic acid is at a concentration of about 3% to about 5% volume to weight or volume to volume as a monobasic acid.

17. A kit for detecting the presence of excessive lead in a surface, the kit comprising:
   pieces of an absorbent material;
   an aqueous solution of a suitable acid;
   distilled or deionized water; and
   a chromogen which visibly changes colors when excessive lead is present in said surface.

18. The kit of claim 17, wherein said acid is citric acid, formic acid, or a mixture thereof.

19. The kit of claim 17, wherein said chromogen comprises rhodizonic acid dipotassium salt.

20. The kit of claim 19, wherein said acid is citric acid.

21. A kit for detecting the presence of excessive lead in a surface, the kit comprising:
   pieces of an absorbent material;
   an aqueous solution of a suitable acid; and
   a stable aqueous solution of a chromogen which visibly changes colors when excessive lead is in said surface.

22. The kit of claim 21, wherein said acid is citric acid, formic acid, or a mixture thereof.

* * * * *